United States Patent [19]
Burns et al.

[11] Patent Number: 5,646,327
[45] Date of Patent: Jul. 8, 1997

[54] METHOD FOR PREPARING HYDROXYLAMINES USING VINYLIC COMPOUNDS WITHOUT BASE NEUTRALIZATION AND REACTION MIXTURE PRODUCED THEREBY

[75] Inventors: Elizabeth Gertrude Burns, Rochester; Lynda Woedy McGarry, North Chili; Gary Stephen Proehl; Lee Hamilton Latimer, both of Rochester, all of N.Y.

[73] Assignee: Eastman Kodak Company, Rochester, N.Y.

[21] Appl. No.: 569,643

[22] Filed: Dec. 8, 1995

[51] Int. Cl.$^6$ .................. C07C 255/00; C07C 205/00; C07C 229/00; C07F 9/22
[52] U.S. Cl. .................. 558/452; 560/23; 560/170; 562/11; 562/45; 562/104; 562/433; 562/107; 564/157; 564/193; 564/301
[58] Field of Search .................. 562/11, 45, 104, 562/433, 107; 560/23, 170; 564/157, 193, 301; 558/452

[56] References Cited

U.S. PATENT DOCUMENTS

| | | | |
|---|---|---|---|
| 3,287,125 | 11/1966 | Green et al. | 96/29 |
| 3,362,961 | 1/1968 | Green et al. | 260/294.7 |
| 3,455,916 | 7/1969 | Green et al. | 260/243 |
| 3,467,711 | 9/1969 | Bader et al. | 260/583 |
| 3,491,151 | 1/1970 | Bader | 260/584 |
| 3,655,764 | 4/1972 | Bader et al. | 260/584 |
| 3,778,464 | 12/1973 | Klemchuk | 260/482 |
| 3,806,345 | 4/1974 | Willems et al. | 96/66 |
| 4,876,174 | 10/1989 | Ishikawa et al. | 430/380 |
| 5,110,985 | 5/1992 | Hayakawa et al. | 562/571 |
| 5,248,811 | 9/1993 | Morimoto | 562/102 |
| 5,262,563 | 11/1993 | Morimoto | 562/104 |
| 5,354,646 | 10/1994 | Kobayashi et al. | 430/372 |

OTHER PUBLICATIONS

Distler, *Angew. Chem. internat. Edit.*, vol. 4(4), pp. 300–311 (1965).
Aurich, et al. (Chem. Ber. (118) 1086–104) 1985.
Aston, et al. (Heterocycles, 28(2) 1015–35) 1989.

*Primary Examiner*—Joseph Conrad
*Attorney, Agent, or Firm*—J. Lanny Tucker

[57] ABSTRACT

Substituted hydroxylamines useful in photographic processing solution can be prepared by reacting a hydroxylamine with a vinylic compound having an electron withdrawing substituent in a suitable solvent, in the absence of a neutralizing base. The resulting products can be used without isolation from the reaction solution.

24 Claims, No Drawings

METHOD FOR PREPARING HYDROXYLAMINES USING VINYLIC COMPOUNDS WITHOUT BASE NEUTRALIZATION AND REACTION MIXTURE PRODUCED THEREBY

FIELD OF THE INVENTION

This invention relates to a method for preparing mono- and disubstituted hydroxylamines that are useful as antioxidants in various photographic processing solutions. The invention also relates to a reaction mixture produced by the method containing the desired product. The reaction mixture can be used in photographic processing solutions without isolation of the hydroxylamine products.

BACKGROUND OF THE INVENTION

Various synthetic methods for making substituted hydroxylamines useful in photographic processing solutions are known, for example, in U.S. Pat. No. 3,287,125 (Green et al), U.S. Pat. No. 3,778,464 (Klemchuk), U.S. Pat. No. 4,876,174 (Ishikawa et al) and U.S. Pat. No. 5,354,646 (Kobayashi et al).

More specific synthetic methods for producing carboxyalkyl substituted hydroxylamines are described in U.S. Pat. No. 5,110,985 (Hayakawa et al). The preferred method involves reacting an $\alpha,\beta$-unsaturated carboxylic acid with a mono-substituted hydroxylamine in a variety of solvents, including water and mixtures of water and water-miscible solvents. The hydroxylamines are preferably used in the form of hydrochlorides or sulfates that must be neutralized with a base (such as sodium hydroxide, sodium carbonate or pyridine). The resulting substituted hydroxylamine product is isolated from the reaction mixture prior to use. Undesirable by-products also are produced, this being another reason for isolation of the desired hydroxylamine product prior to use.

Related U.S. Pat. No. 5,248,811 (Morimoto et al) and U.S. Pat. No. 5,262,563 (Morimoto et al) describe various syntheses of sulfoalkyl-substituted hydroxylamines. In the preferred synthesis, a mono-substituted hydroxylamine hydrochloride or sulfate is reacted with a vinylsulfonate. Unwanted by-products are allegedly suppressed, but the desired product must be isolated using salt precipitation or ion exchange resins. The reaction is carried out in the presence of a neutralizing base which produces unwanted salts that must be removed by filtration.

It would be desirable to have a simple method for preparing substituted hydroxylamines that need not be isolated prior to use, but can be immediately used in photographic processing solutions. Thus, it is also desired to suppress the formation of significant amounts of unwanted by-products.

SUMMARY OF THE INVENTION

The problems with known synthetic methods have been overcome with a method for preparing a hydroxylamine of the general structure (I):

HO—NR—L wherein

R is hydrogen, an alkyl group of 1 to 12 carbon atoms or L,

L has the general structure (II):

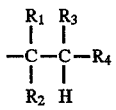

wherein $R_1$ and $R_2$ are independently hydrogen or an alkyl group, $R_3$ is hydrogen, halo or an alkyl group, and $R_4$ is sulfo, or —$CONR_5R_6$ wherein $R_5$ and $R_6$ are independently hydrogen or an alkyl group of 1 to 4 carbon atoms, —$COOR_7$ wherein $R_7$ is hydrogen or an alkyl group of 1 to 4 carbon atoms, phosphono, cyano, or a phenyl group substituted with one or more sulfo, —$CONR_5R_6$, phosphono, cyano, or —$COOR_7$ groups, comprising reacting a vinylic compound having the structure (III):

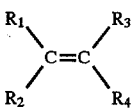

wherein $R_1$, $R_2$, $R_3$ and $R_4$ are defined above, with a hydroxylamine having the structure HO-NHR wherein R is defined above, the reacting step taking place in water or a water-miscible organic solvent, or mixture thereof, in the absence of a neutralizing base.

The invention also provides a reaction solution comprising the hydroxylamine of the general structure (I) above, the hydroxylamine having been prepared by reacting, without isolation, the vinylic compound having the structure (III) above with a hydroxylamine having the structure HO-NHR wherein R is defined above, the reacting step taking place in water or a water-miscible organic solvent, or mixture thereof, in the absence of a neutralizing base.

This invention provides a simple method for preparing a wide variety of substituted hydroxylamines without the need to use neutralizing bases that tend to produce unwanted by-products (such as salts) that require isolation. This feature allows the preparation and use of the desired product, in situ, that is without the need for actual isolation from the reaction solution. It is also an advantage that the process can be carried out at any desired temperature and any desired pH. Thus, the pH need not be significantly adjusted prior to use of the solution, for example, in photographic processing solutions.

DETAILED DESCRIPTION OF THE INVENTION

In structure (I) described herein, R is hydrogen, an alkyl group of 1 to 12 carbon atoms, or the group "L". By alkyl group is meant a substituted or unsubstituted, branched or linear alkyl radical having up to 12 carbon atoms in the branched or linear chain.

Preferably, R is hydrogen or an alkyl group of 1 to 5 carbon atoms. More preferably, it has 3 to 5 carbon atoms and is branched at the carbon atom directly attached to the nitrogen atom of the hydroxylamine molecule. Representative alkyl groups include, but are not limited to, methyl, ethyl, n-propyl, isopropyl, n-butyl, t-butyl, 2-methyl-1-propyl, n-pentyl, 2-ethyl-1-propyl, 2-methyl-3-methyl-1-pentyl, n-hexyl, n-octyl, n-decyl, n-dodecyl, benzyl, 2-cyclohexylethyl, and others readily apparent to one skilled in the art. Preferred alkyl groups are isopropyl, 2-methyl-1-propyl, 2-ethyl-1-propyl, 2-methyl-1-butyl and similar groups which are further substituted with groups other than alkyl groups (defined below). Most preferably, R is isopropyl.

R can also be "L" which is defined by structure (II) wherein $R_1$, $R_2$ and $R_3$ are independently hydrogen, or an alkyl group of 1 to 4 carbon atoms (including those examples defined above for R). The alkyl group can also be substituted as described in general below. In addition, $R_3$ can be a halo group (such as bromo or chloro), or an alkyl group of 1 to 4 carbon atoms which is substituted with one or more halo, carboxy, sulfo or other electron withdrawing groups as defined below. Preferably, each of $R_1$, $R_2$ and $R_3$ is hydrogen or an alkyl group of 1 to 3 carbon atoms (both branched and linear, substituted or unsubstituted). More preferably, each of $R_1$, $R_2$ and $R_3$ is hydrogen or methyl, and most preferably, each is hydrogen.

$R_4$ is an electron withdrawing group as defined by a Hammett sigma value equal to or greater than about 0.1. For example, it can be sulfo (free acid or salts thereof). By salts is meant alkali metal, alkaline earth metal or ammonium (including alkyl- or arylsubstituted ammonium) salts. In addition, $R_4$ can be the amido group —$CONR_5R_6$ wherein $R_5$ and $R_6$ are independently hydrogen or an alkyl group of 1 to 4 carbon atoms (substituted or unsubstituted, linear or branched). Preferably, $R_5$ and $R_6$ are independently hydrogen or an alkyl group of 1 to 3 carbon atoms. More preferably, each is hydrogen or methyl.

$R_4$ can also be phosphono, cyano, or —$COOR_7$ wherein $R_7$ is hydrogen or an alkyl group of 1 to 4 carbon atoms (substituted or unsubstituted, linear or branched as defined herein). Preferably, $R_7$ is hydrogen so that $R_4$ is carboxy (free acid or salts thereof as defined above for sulfo), methyl or ethyl. Most preferably, $R_7$ is hydrogen.

Further, $R_4$ can be a phenyl group having one or more of the electron withdrawing groups defined above for $R_4$.

Preferably, $R_4$ is hydrogen, an alkyl group of 1 to 4 carbon atoms (linear or branched, substituted or unsubstituted), carboxy, sulfo (as defined above) or the amido group —$CONR_5R_6$ wherein each of $R_5$ and $R_6$ is hydrogen or an alkyl group of 1 to 3 carbon atoms (such as methyl, ethyl, n-propyl and isopropyl). In one embodiment, both of $R_5$ and $R_6$ are hydrogen, methyl or ethyl. More preferably, $R_4$ is either carboxy or sulfo with sulfo being most preferred.

Unless otherwise specifically stated, the alkyl and phenyl groups defined above can be further substituted with one or more substituents which do not destroy properties essential for participation in the reaction of the present invention, or for their use in photographic processing solutions. Especially useful substituents are electron withdrawing groups, but electron donating groups can also be used as substituents as long as the entire radical has a cumulative electron withdrawing nature. Thus, when the term "group" is used in a definition, it means that one or more hydrogen atoms from a carbon, or nitrogen atom has been substituted with, for example, halo (chloro, bromo and the like), nitro, hydroxy, cyano, carboxy, sulfo, an alkenyl group, an alkynyl group, an amino group, an amido group, an alkoxy group, an aryl group, and aryloxy group, a carbonamido group, a sulfonamido group, a carbamoyl group, a sulfamoyl group, an acyl group, an imino group, phosphono (free acid or salt thereof), or a heterocyclic ring. Such groups would be readily apparent to one skilled in the art, and that person would also realize that any such substituents can be further substituted with the same or different substituents if desired.

The reaction of the hydroxylamine having the structure HO-NHR and the vinylic compound having structure (III) is carried out in water, a low alcohol or another water-miscible organic solvent (such as methanol, ethanol, n-propanol, isopropanol or n-butanol, N-methyl pyrrolidone, tetrahydrofuran, N,N-dimethylacetamide, N,N-dimethylformamide or dimethylsulfoxide), or mixtures of two or more of these. Water and the lower alcohols noted above, and tetrahydrofuran, or mixtures of any of these are preferred, with water and methanol or mixtures thereof being most preferred.

The amount of hydroxylamine reactant used in the reaction is generally at least about 1 mol/l, with from about 2 to about 20 mol/l being preferred. The vinylic compound is then present in amounts of at least about 0.5 times the molar amount of hydroxylamine, with from about 1 to about 3 times the molar amount being preferred, and from about 1 to about 2 times being most preferred. The reactants can be mixed by simultaneous addition to the reaction solvent, or one can be added to the other, or added to the reaction solvent sequentially. A skilled artisan would be aware of the suitable reaction procedures, especially in view of the representative working examples provided below.

The reaction temperature can be from about 0° to about 100° C., with from about 20° to about 100° C. being preferred. Optimal reaction temperature will depend upon various conditions, including reactants, solvents, pH and other conditions readily apparent to one skilled in the art. Routine experimentation can be carried out to determine the optimum reaction temperature.

Similarly, the time of reaction can be varied depending upon the reactants, but it is generally at least about 2 hours, with from about 2 to about 24 hours being preferred. The progress of reaction can be determined by taking samples for analysis periodically, such as by using NMR.

The reaction mixture can have any desirable pH less than about 10.

As used herein, the term "about" in defining times and amounts refers to ±20% of the indicated value. In reference to pH, it refers to ±0.5 pH unit, and in reference to temperature, it refers to ±5° C.

One advantage of this invention is that the product need not be isolated from the reaction mixture prior to use in photographic processing solutions (for example, color developer, bleaching, bleach/fixing or stabilizing solutions). However, if isolation is desired for some reason, it can be done by conventional means such as filtration, solvent evaporation, solvent extraction or precipitation.

Particularly useful compounds prepared using the present invention are bis(2-ethanesulfonic acid)hydroxylamine, N-isopropyl-N-(2-ethanesulfonic acid)hydroxylamine, bis (3-propionic acid)hydroxylamine, N-isopropyl-N-(3-propionic acid)hydroxylamine, N,N-bis(N,N-dimethylamidoethyl)hydroxylamine, bis-N-(2-carboxyethyl)hydroxylamine, dimethylester, bis-N-(2-carboxyethyl)hydroxylamine, diethylester, N-(2-carboxyethyl)-N-hydroxy-β-alanine, N-isopropyl-N-(2-carboxymethylene-3-propionic acid)hydroxylamine, bis(2-carboxymethylene-3-propionic acid)hydroxylamine, N-isopropyl-N-(sulfonamidoethyl)hydroxylamine, N-isopropyl-N-(N,N-dimethylsulfonamidoethyl) hydroxylamine, bis(N,N-dimethylsulfonamidoethyl) hydroxylamine, N-isopropyl-N-(N,N-diethylsulfonamidoethyl)hydroxylamine and bis(N,N-diethylsulfonamidoethyl)hydroxylamine and salts thereof (where possible).

The following examples illustrate the practice of the present invention, but the invention is not to be interpreted as limited thereto. Unless otherwise noted, all percentages are by weight.

Materials and Methods for Examples:

Unless otherwise noted, all starting materials or reagents are readily available from Eastman Kodak Company or another commercial source, or readily prepared using conventional reagents and conditions. Free hydroxylamine, for example, is available in an aqueous solution from the Howard Hall Division of R. W. Greefe & Co., Inc. (Greenwich, Conn.).

EXAMPLE 1

Preparation of N-isopropyl-N-(2-ethanesulfonic acid)hydroxylamine, Sodium Salt

This material was prepared using the preferred method of this invention.

An aqueous solution (420 ml) of vinylsulfonic acid, sodium salt (25%) was heated to reflux. While at reflux, an aqueous solution (480 g) of isopropyl hydroxylamine was linearly added over a period of two hours. During the next five hours, water (600 g) was removed linearly by distillation. After cooling the reaction solution to 20° C., isopropanol (500 ml) was added with good mechanical stirring to keep the resulting white solid suspended. This solid was collected on a sintered glass funnel, rinsed with additional fresh isopropanol (100 ml), and dried overnight at 50° C. under vacuum for analysis. N-isopropyl-N-(2-ethanesulfonic acid)hydroxylamine, sodium salt was isolated as a white powder. However, the product could have been left in the reaction solution for later use if desired.

All analyses were consistent with the structure of the desired compound. The $^1$H NMR in $D_2O$ had peaks at 4.8 (NOH), 3.2–2.9 (isopropyl methine and two methylenes of the ethylsulfonato sodium salt moiety), and 1.1 ppm (two methyls of the isopropyl group). The $^{13}C$ NMR had peaks at 59.4, 52.4, 49.9 and 19.2 ppm. The sodium analysis was 11.5%.

EXAMPLE 2

Preparation of Bis(2-ethanesulfonic acid) hydroxylamine, Disodium Salt

An aqueous solution (150 ml) of vinylsulfonic acid, sodium salt (25%) was heated to 70° C. over a period of 30 minutes. While the solution was stirred, an aqueous solution (10.3 g) of hydroxylamine (50%) was linearly added over a period of 5 minutes. The reaction solution was held at 70° C. for eight hours, then cooled to 20° C. over a period of 30 minutes. To the reaction solution was then added methanol (800 ml) over a period of 5 minutes. After an additional 30 minutes, the resulting solid product was collected on a filter funnel, rinsed with fresh methanol (100 ml), and dried overnight at 50° C. under vacuum to give 49 g of white solid for analysis.

The analyses were consistent with the structure of the desired product. The $^1$H NMR in $D_2O$ had peaks at 4.8 (NOH), and 4.7 and 3.2 ppm for the two different methylene protons in the molecule. The $^{13}C$ NMR had peaks at 56.4 and 49.8 ppm for the methylene carbons in the molecule. The sodium analysis was 15.1% (consistent for the monohydrate).

EXAMPLE 3

Preparation of N-isopropyl-N-(3-propionic Acid) hydroxylamine

Acrylic acid (120 g) was added to an aqueous solution (825 g) of isopropylhydroxylamine (15%) and methanol (1250 ml) at room temperature with vigorous mechanical stirring. Upon completion of the addition, the reaction solution was heated to 60° C. and maintained at that temperature overnight. Upon cooling to room temperature and concentration of the reaction solution by evaporation, a yellow oil crystallized upon standing. Isopropanol and ether were added to facilitate collection of the resulting product by suction filtration for analysis. The resulting white granular solid was dried overnight under vacuum to give 155 g.

The analyses were consistent with the desired structure. The $^1$H NMR in dimethylsulfoxide-d6 had peaks at 7.0 (NOH), 2.7 (isopropyl methine plus methylene group of the propionic acid moiety), 2.35 (methylene of propionic acid moiety), and 0.9 ppm (two methyls of the isopropyl group). The mass spectrum was consistent with the desired compound.

EXAMPLE 4

Preparation of N,N-Bis(N,N-dimethylamidoethyl) hydroxlamine

Methanol (200 ml) was added to a methanically stirred aqueous solution (66 g) of hydroxylamine (50%). N,N-dimethylacrylamide (198 g) was added dropwise to the resulting cloudy suspension over a period of several hours. The reaction solution became warm and clear. Upon cooling to 50° C., the reaction mixture became an orange, viscous mixture, which was transferred to another vessel and allowed to cool to room temperature. After 14 hours, the mixture had solidified. The solid was collected and dried under vacuum overnight to give 105 g of white solid for analysis.

All analyses were consistent with the desired structure. The 1H NMR spectrum in dimethylsulfoxide-d6 had peaks at 7.8 (NOH), 2.9, 2.7 (amide methyl groups), 2.73 (methylene group) and 2.43 (methylene group).

EXAMPLE 5

Preparation of Bis-N-(2-carboxyethyl) hydroxylamine, Dimethylester

Methanol (200 ml) was added to a mechanically stirred aqueous solution of hydroxylamine (13.24 g of 50% solution, 0.2 moles). Methyl acrylate (34.44 ml, 0.4 moles) was added dropwise to the solution at 25° C. over thirty minutes as the solution became warm during the resulting reaction. After completion of the addition, the reaction mixture was heated to 60° C. in an oil bath and stirred overnight. The pH of the resulting mixture was 6.15. The solution was then cooled to room temperature, and concentrated at 40° C. under reduced pressure to yield a pale yellow, cloudy oil (41.6 g, 99%).

All analyses of the oil were consistent with the desired structure. The $^1$H NMR spectrum in dimethylsulfoxide-d6 had peaks at 7.9 (NOH), 3.54 (s,6H), 2.75 (t,4H), and 2.45 (t,4H).

EXAMPLE 6

Preparation of Bis-N-(2-Carboxyethyl) hydroxylamine, Diethylester

Methanol (200 ml) was added to a mechanically stirred aqueous solution of hydroxylamine (13.24 g of 50% solution, 0.2 moles). Ethyl acrylate (43.34 ml, 0.4 moles) was added dropwise to the solution at 25° C. over thirty minutes as the solution became warm during the resulting reaction. After completion of the addition, the reaction mixture was heated to 60° C. in an oil bath and stirred overnight. The pH of the resulting mixture was 6.5. The solution was then cooled to room temperature, and concentrated at 40° C. under reduced pressure to yield a pale yellow, cloudy oil (46.3 g, 99%).

All analyses of the oil were consistent with the desired structure. The $^1$H NMR spectrum in dimethylsulfoxide-d6 had peaks at 7.9 (NOH), 4.0 (q, 4H), 2.75 (t,4H), 2.40 (t,4H), and 1.1 (t,6H).

EXAMPLE 7

Preparation of N-(2-carboxyethyl)-N-hydroxy-β-Alanine

Methanol (200 ml) was added to a mechanically stirred aqueous solution of hydroxylamine (13.24 g of 50% solution, 0.2 moles). Acrylic acid (27.4 ml, 0.4 moles) was added dropwise to the solution at 25° C. over thirty minutes. After a few hours of reaction, a white precipitate began to form. The reaction mixture was stirred overnight at room temperature, and the resulting white solid was filtered out, washed with cold water, and dried in vacuum overnight to give 30.4 g (85%) of the desired compound.

All analyses of the solid were consistent with the desired structure. The $^1$H NMR spectrum in dimethylsulfoxide-d6 had peaks at 5.0 (br.s), 2.7 (t,4H) and 2.35 (t,4H), and a melting point of 148°–149° C.

EXAMPLE 8

Preparation of N-isopropyl-N-(2-carboxymethylene-3-propionic acid)hydroxylamine

Methanol (300 ml) was added to an aqueous 15% solution (400 ml) of N-isopropylhydroxylamine (0.8 moles), followed by addition of itaconic acid (104 g, 0.8 moles) in 3 portions as a solid. Additional methanol (100 ml) was used to rinse the itaconic acid into the flask. After all of the solid acid had dissolved, the mixture was stirred at room temperature for 6 days, and filtered to collect the resulting white solid product. This material was dried under mild vacuum to a weight of 142 g (m.p. 136°–8° C.). NMR analysis was consistent with the structure of the desired compound.

Similarly, bis(2-carboxymethylene-3-propionic acid) hydroxylamine, N-isopropyl-N-(sulfonamidoethyl) hydroxylamine, N-isopropyl-N-(N,N-dimethylsulfonamidoethyl)hydroxylamine, bis(N,N-dimethylsulfonamidoethyl)hydroxylamine, N-isopropyl-N-(N,N-diethylsulfonamidoethyl)hydroxylamine and bis(N,N-diethylsulfonamidoethyl)hydroxylamine were prepared using similar conditions and slightly varying solvent mixtures of water and methanol, water and tetrahydrofuran or tetrahydrofuran and N,N-dimethylformamide. The exact solvent mixtures could be readily determined by a skilled worker in the art. These compounds were prepared by reacting itaconic acid, vinylsulfonamide, N,N-dimethyl vinylsulfonamide or N,N-diethyl vinylsulfonamide with hydroxylamine or N-isopropylhydroxylamine, as would be appropriate.

Comparative Experiment:

An attempt was made to reproduce Example 8 of U.S. Pat. No. 5,248,811 (noted above) to produce bis(ethylsulfonic acid)hydroxylamine, sodium salt from hydroxylamine and sodium vinylsulfonate, without the presence of a neutralizing base, such as sodium hydroxide. The desired product was not obtained. Rather, mass spectroscopic analysis showed that vinylsulfonic acid, sodium salt (28 g) was produced.

The invention has been described in detail with particular reference to preferred embodiments thereof, but it will be understood that variations and modifications can be effected within the spirit and scope of the invention.

We claim:

1. A method for preparing a hydroxylamine of the general structure (I):

HO—NR—L wherein

R is hydrogen, an alkyl group of 1 to 12 carbon atoms or L,

L has the general structure (II):

$$-\underset{\underset{R_2}{|}}{\overset{\overset{R_1}{|}}{C}}-\underset{\underset{H}{|}}{\overset{\overset{R_3}{|}}{C}}-R_4$$

wherein $R_1$ and $R_2$ are independently hydrogen or an alkyl group, $R_3$ is hydrogen, halo or an alkyl group, and $R_4$ is sulfo, —CONR$_5$R$_6$ wherein R$_5$ and R$_6$ are independently hydrogen or an alkyl group of 1 to 4 carbon atoms, —COOR$_7$ wherein R$_7$ is hydrogen or an alkyl group of 1 to 4 carbon atoms, phosphono, cyano, or a phenyl group substituted with one or more sulfo, —CONR$_5$R$_6$, phosphono, cyano, or —COOR$_7$ groups, comprising reacting a vinylic compound having the structure (III):

$$\underset{R_2}{\overset{R_1}{\diagdown}}C=C\underset{R_4}{\overset{R_3}{\diagup}}$$

wherein $R_1$, $R_2$, $R_3$ and $R_4$ are defined above, with a hydroxylamine having the structure HO-NHR wherein R is defined above, said reacting step taking place in a reaction solvent that is water or a water-miscible organic solvent, or mixture thereof, in the absence of a neutralizing base.

2. The method of claim 1 wherein R is hydrogen, an alkyl group of 1 to 5 carbon atoms, or L.

3. The method of claim 2 wherein R is L wherein $R_1$ and $R_2$ are independently hydrogen or a methyl group, $R_3$ is hydrogen, and $R_4$ is carboxy, sulfo or —CONR$_5$R$_6$.

4. The method of claim 2 wherein R is an alkyl group of from 3 to 5 carbon atoms and is branched at the carbon directly attached to the nitrogen atom.

5. The method of claim 4 wherein R is isopropyl.

6. The method of claim 1 wherein $R_1$ and $R_2$ are independently hydrogen or an alkyl group of 1 to 4 carbon atoms, $R_3$ is hydrogen or a methyl group, and $R_4$ is carboxy, sulfo or —CONR$_5$R$_6$ wherein each of R$_5$ and R$_6$ is independently hydrogen or an alkyl group of 1 to 3 carbon atoms.

7. The method of claim 6 wherein $R_4$ is carboxy or sulfo.

8. The method of claim 7 wherein R is L, and $R_4$ in each occurrence is carboxy, sulfo or dimethylamido.

9. The method of claim 7 wherein $R_1$ and $R_2$ are each hydrogen or methyl, and $R_3$ is hydrogen.

10. The method of claim 8 wherein R is hydrogen or an alkyl group having 3 to 5 carbon atoms that is branched at the carbon attached to the nitrogen atom.

11. The method of claim 1 wherein the hydroxylamine of general structure (I) is bis(2-ethanesulfonic acid) hydroxylamine, N-isopropyl-N-(2-ethanesulfonic acid) hydroxylamine, bis(3-propionic acid)hydroxylamine, N-isopropyl-N-(3-propionic acid)hydroxylamine, N,N-bis (N,N-dimethylamidoethyl)hydroxylamine, bis-N-(2-carboxyethyl)hydroxylamine dimethylester, bis-N-(2-carboxyethyl)hydroxylamine diethylester, N-(2-carboxyethyl)-N-hydroxy-β-alanine, N-isopropyl-N-(2-carboxymethylene-3-propionic acid)hydroxylamine, bis(2-carboxymethylene-3-propionic acid)hydroxylamine, N-isopropyl-N-(sulfonamidoethyl)hydroxylamine, N-isopropyl-N-(N,N-dimethylsulfonamidoethyl)-hydroxylamine, bis(N,N-dimethylsulfonamidoethyl)-hydroxylamine, N-isopropyl-N-(N,N-diethylsulfonamidoethyl)hydroxylamine or bis (N,N-diethylsulfonamidoethyl)hydroxylamine.

12. The method of claim 1 wherein said reacting step is carried out in water, a lower alcohol, tetrahydrofuran, N,N-dimethylformamide, N,N-dimethylacetamide, N-methyl pyrrolidone, dimethylsulfoxide, or a mixture of two or more of these.

13. The method of claim 1 wherein after preparing said hydroxylamine of general structure (I), it is isolated from said reaction solvent.

14. A reaction solution comprising a hydroxylamine of the general structure (I):

HO—NR—L wherein

R is hydrogen, an alkyl group of 1 to 12 carbon atoms or L,

L has the general structure:

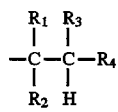

wherein $R_1$ and $R_2$ are independently hydrogen or an alkyl group, $R_3$ is hydrogen, halo or an alkyl group, and $R_4$ is sulfo, or —$CONR_5R_6$ wherein $R_5$ and $R_6$ are independently hydrogen or an alkyl group of 1 to 4 carbon atoms, —$COOR_7$ wherein $R_7$ is hydrogen or an alkyl group of 1 to 4 carbon atoms, phosphono, cyano, or a phenyl group substituted with one or more sulfo, —$CONR_5R_6$, phosphono, cyano, or —$COOR_7$ groups, said hydroxylamine having been prepared by reacting, without isolation, a vinylic compound having the structure (III):

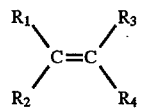

wherein $R_1$, $R_2$, $R_3$ and $R_4$ are defined above, with a hydroxylamine having the structure HO-NHR wherein R is defined above, said reacting step taking place in water or a water-miscible organic solvent, or mixture thereof, in the absence of a neutralizing base.

15. The reaction solution of claim 14 wherein R is hydrogen, an alkyl group of 1 to 5 carbon atoms, or L.

16. The reaction solution of claim 15 wherein R is L wherein $R_1$ and $R_2$ are hydrogen or a methyl group, $R_3$ is hydrogen, and $R_4$ is carboxy, sulfo or —$CONR_5R_6$.

17. The reaction solution of claim 15 wherein R is an alkyl group of from 3 to 5 carbon atoms and is branched at the carbon attached to the nitrogen atom.

18. The reaction solution of claim 17 wherein R is isopropyl.

19. The reaction solution of claim 14 wherein $R_1$ and $R_2$ are independently hydrogen or an alkyl group of 1 to 4 carbon atoms, $R_3$ is hydrogen, and $R_4$ is carboxy, sulfo or —$CONR_5R_6$ wherein each of $R_5$ and $R_6$ is independently hydrogen or an alkyl group of 1 to 3 carbon atoms.

20. The reaction solution of claim 19 wherein $R_4$ is carboxy or sulfo.

21. The reaction solution of claim 20 wherein R is L, and $R_4$ in each occurrence is carboxy, sulfo or dimethylamido.

22. The reaction solution of claim 20 wherein $R_1$ and $R_2$ are each hydrogen or methyl.

23. The reaction solution of claim 20 wherein R is hydrogen or an alkyl group having 3 to 5 carbon atoms that is branched at the carbon directly attached to the nitrogen atom.

24. The reaction solution of claim 14 wherein the hydroxylamine of general structure (I) is bis(2-ethanesulfonic acid)hydroxylamine, N-isopropyl-N-(2-ethanesulfonic acid)hydroxylamine, bis(3-propionic acid) hydroxylamine, N-isopropyl-N-(3-propionic acid) hydroxylamine or N,N-bis(N,N-dimethylamidoethyl) hydroxylamine, bis-N-(2-carboxyethyl)hydroxylamine dimethylester, bis-N-(2-carboxyethyl)hydroxylamine diethylester, N-(2-carboxyethyl)-N-hydroxy-β-alanine, N-isopropyl-N-(2-carboxymethylene-3-propionic acid) hydroxylamine, bis(2-carboxymethylene-3-propionic acid) hydroxylamine, N-isopropyl-N-(sulfonamidoethyl) hydroxylamine, N-isopropyl-N-(N,N-dimethylsulfonamidoethyl)-hydroxylamine, bis(N,N-dimethylsulfonamidoethyl)-hydroxylamine, N-isopropyl-N-(N,N-diethylsulfonamidoethyl)hydroxylamine or bis(N,N-diethylsulfonamidoethyl)hydroxylamine.

* * * * *

UNITED STATES PATENT AND TRADEMARK OFFICE
CERTIFICATE OF CORRECTION

PATENT NO. : 5,646,327
DATED : July 8, 1997
INVENTOR(S) : Elizabeth Gertrude Burns et al It is certified that error appears in the above-indentified patent and that said Letters Patent is hereby corrected as shown below:

Title page, Col. 1, after [22] insert

--Related U.S. Application Data
[60] Provisional Application Serial No. 60/002,789 filed 25 August 1995, and US 60/003,311 filed 06 September 1995.--

Col. 1, line 6, insert

--Cross Reference to Related Application
Reference is made to and priority claimed from U.S. Provisional Application Serial No. US 60/002,789 filed 25 August 1995, and US 60/003,311 filed 06 September 1995, entitled METHOD FOR PREPARING HYDROXYLAMINES USING VINYLIC COMPOUNDS WITHOUT BASE NEUTRALIZATION AND REACTION MIXTURE PRODUCED THEREBY.--

Signed and Sealed this

Fourteenth Day of October, 1997

*Attest:*

BRUCE LEHMAN

*Attesting Officer*   *Commissioner of Patents and Trademarks*